(12) United States Patent
Raines et al.

(10) Patent No.: US 8,557,856 B2
(45) Date of Patent: Oct. 15, 2013

(54) ETOMIDATE ANALOGUES WITH IMPROVED PHARMACOKINETIC AND PHARMACODYNAMIC PROPERTIES

(75) Inventors: Douglas E. Raines, Wayland, MA (US); Stuart A. Forman, Arlington, MA (US); Keith W. Miller, Lincoln, MA (US); Syed Shaukat Husain, Newton, MA (US); Joseph F. Cotten, Grafton, MA (US)

(73) Assignee: The General Hospital Corporation, Boston, MA (US)

( * ) Notice: Subject to any disclaimer, the term of this patent is extended or adjusted under 35 U.S.C. 154(b) by 426 days.

(21) Appl. No.: 12/935,086

(22) PCT Filed: Mar. 31, 2009

(86) PCT No.: PCT/US2009/038872
§ 371 (c)(1), (2), (4) Date: Nov. 11, 2010

(87) PCT Pub. No.: WO2009/146024
PCT Pub. Date: Dec. 3, 2009

(65) Prior Publication Data
US 2011/0053998 A1     Mar. 3, 2011

Related U.S. Application Data

(60) Provisional application No. 61/040,911, filed on Mar. 31, 2008.

(51) Int. Cl.
*A61K 31/4174* (2006.01)
*C07D 233/90* (2006.01)

(52) U.S. Cl.
USPC .................. 514/400; 548/334.5; 548/341.5

(58) Field of Classification Search
USPC ..................... 548/334.5, 341.5; 514/400
See application file for complete search history.

(56) References Cited

U.S. PATENT DOCUMENTS

| | | | |
|---|---|---|---|
| 3,354,173 A | 11/1967 | Godefroi et al. | |
| 4,038,286 A | 7/1977 | Roevens et al. | |
| 4,289,783 A | 9/1981 | Mesens | |
| 5,019,583 A | 5/1991 | Feldman et al. | |
| 5,466,700 A | 11/1995 | Batenhorst et al. | |
| 7,189,859 B2 * | 3/2007 | Zolle et al. | 548/334.5 |
| 2003/0055023 A1 | 3/2003 | Rajewski et al. | |

FOREIGN PATENT DOCUMENTS

| EP | 277384 A2 * | 8/1988 |
|---|---|---|
| EP | 0289066 A1 | 11/1988 |
| WO | 96/39137 A1 | 12/1996 |
| WO | WO 2007144725 A2 * | 12/2007 |

OTHER PUBLICATIONS

Chivikas, C.J., et al., "Phenacyl-Directed Alkylation of Imidazoles: A New Regiospecific Synthesis of 3-Substituted L-Histidines," J. Org. Chem. 1987, 51, 3591-3594.
Husain, S.S., et al., "2-(3-Methyl-3H-diaziren-3-yl)ethyl 1-(1-phenylethyl)-1H-imidazole-5-carboxylate: A Derivative of the Stereoselective General Anesthetic Etomidate for Photolabeling Ligand-Gated Ion Channels," J. Med. Chem. 2003, 46, 1257-1265.
Jagr, M., et al., "Synthesis and Characterization of Styrene Oxide Adducts with Cysteine, Histidine, and Lysine in Human Globin," Chem. Res. Tocicol. 2007, 20, 1442-1452.
Swain, M.D., et al., "Geometric Preferences of Crosslinked Protein-Derived Cofactors Reveal a High Propensity for Near-Sequence Pairs," Proteins: Structure, Function, and Bioinformatics 59:64-71 (2005).
Xu, R., et al., "Rapid Communication: Catecholamine and Histidyl Protein Cross-Linked Structures in Sclerotized Insect Cuticle," Insect Biochem. Molec. Biol. vol. 27, No. 2, pp. 101-108, 1997.
Database zregistry [Online] chemical abstracts; May 21, 1998, XP002669165, Database accession No. 205829-25-0.
De Coster, et al. J. Vet. Pharmacol. Therap. 10:227-232 (1987).
De Coster, et al. J. Vet. Pharmacol. Therap. 11:345-353 (1988).
Godefroi et al. J. Medicinal Chemistry 8(1):220-223 (1964).
Van Dijk, et al. Research in Veterinary Science 42:200-2003 (1987).

* cited by examiner

*Primary Examiner* — Jason M Nolan
(74) *Attorney, Agent, or Firm* — Nixon Peabody LLP

(57) ABSTRACT

The invention is directed to compounds according to formula (I): where $R_1$ is $L_1C(O)OT$ or $L_1C(O)OL_2C(O)OT$; $R_2$ is a substituted or unsubstituted $C_1$-$C_{10}$ alkyl, $C_2$-$C_{10}$ alkenyl, or $C_2$-$C_{10}$ alkynyl, or $R_1$; n is an integer from 0 to 5; each $R_3$ is independently halogen or $R_2$; $L_1$ and $L_2$ are each independently a bond, a substituted or unsubstituted $C_1$-$C_{10}$ alkylene, $C_2$-$C_{10}$ alkenylene, or $C_2$-$C_{10}$ alkynylene; and T is H, a substituted or unsubstituted $C_1$-$C_{10}$ alkyl, $C_2$-$C_{10}$ alkenyl, or $C_2$-$C_{10}$ alkynyl, nitrophenol, or cyclopropyl. The invention is also directed to a pharmaceutical composition comprising a compound according to formula (I) and a pharmaceutically acceptable carrier, and to methods for providing anesthesia in mammals by administering such a pharmaceutical composition.

(I)

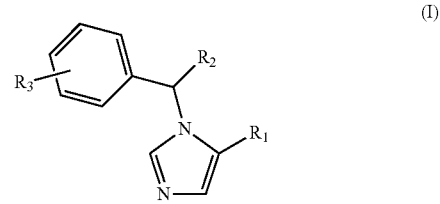

24 Claims, 9 Drawing Sheets

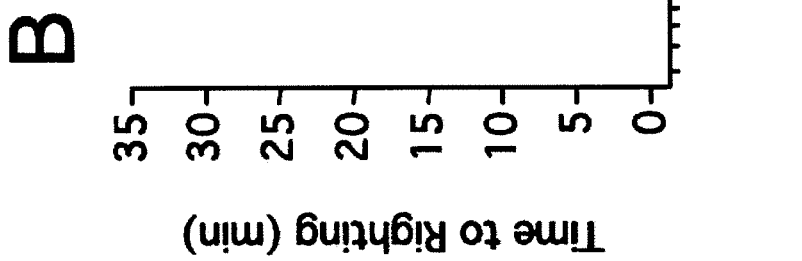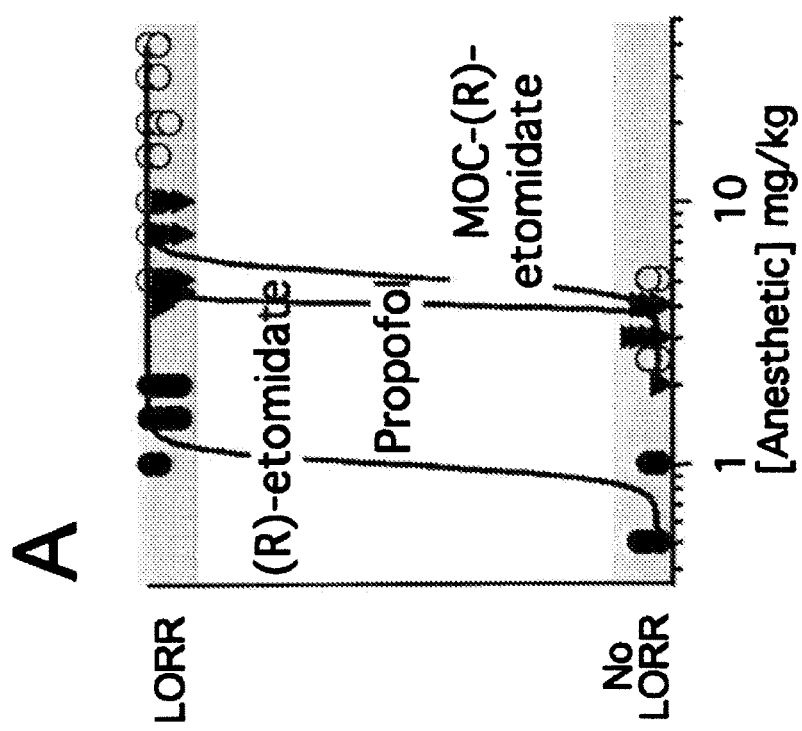
Figures 7A-B

ETOMIDATE ANALOGUES WITH IMPROVED PHARMACOKINETIC AND PHARMACODYNAMIC PROPERTIES

CROSS REFERENCE TO RELATED APPLICATION

This application is a 35 U.S.C. 371 National Stage Application of International Application No. PCT/US2009/038872 filed on Mar. 31, 2009, which designates the United States, and which claims benefit under 35 U.S.C. §119(e) of the U.S. Provisional Application No. 61/040,911 filed Mar. 31, 2008, the contents of which are incorporated herein by reference in its entirety.

GOVERNMENT SUPPORT

The subject matter of this application was made with support from the National Institutes of Health GM058448. The U.S. Government has certain rights in this invention.

FIELD OF THE INVENTION

This invention relates to etomidate analogues that have improved pharmacokinetic and pharmacodynamic properties and their use as anaesthetics.

BACKGROUND OF THE INVENTION

Each year, nearly 30 million general anesthetics are administered in the U.S. alone. At the concentrations required to produce anesthesia, all general anesthetics produce potentially serious and sometimes deadly side effects. Of particular concern is depression of cardiovascular and respiratory function, which can be life threatening, particularly in elderly, sick, and traumatized patients. These deleterious side effects are caused by nearly all general anesthetics and explain why anesthetics have among the lowest therapeutic indices (LD50/ED50) of any class of therapeutic drugs. Therefore, there is great value in developing safer anesthetic agents with fewer side effects.

Etomidate (ethyl 3-(1-phenylethyl)imidazole-4-carboxylate) is a rapidly acting imidazole-based I.V. sedative-hypnotic that can be used to induce and maintain general anesthesia or conscious sedation. It exists as two enantiomers; however, the (R)-enantiomer is ~10-fold more potent an anesthetic than the (S)-enantiomer. The (R)-enantiomer is the one that is used clinically (see Structure 1, below). (R)-etomidate induces loss of righting reflexes in tadpoles (Husain, S. S., et al., *J Med Chem*, 46:1257-1265 (2003)) and loss of responsiveness in humans (Arden, J. R., et al., *Anesthesiology*, 65:19-27 (1986)) at a free-aqueous concentration of ~2 µM.

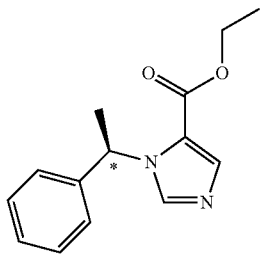 [SMILES: CCOC(=O)c1cncn1[C@H](C)c1ccccc1]

Structure 1—(R)-Etomidate(ethyl 3-(1-phenylethyl) imidazole-4-carboxylate)

At the molecular level, there is compelling evidence that etomidate produces anesthesia by enhancing the function of $GABA_A$ receptors containing $\beta_2$ or $\beta_3$ subunits. Etomidate enhances GABA receptor-mediated currents evoked by low concentrations of agonist, but minimally enhances currents evoked by high concentrations of agonist. This shifts the agonist concentration-response curve leftward (reduces the agonist EC50). Etomidate also directly activates $GABA_A$ receptors in the absence of agonist.

Compared to other general anesthetics, etomidate has an unusually high therapeutic index; (R)-etomidate's therapeutic index in animals is 26.4 compared to 4.6 and 3.1 for thiopental and propofol, respectively (Janssen, P. A., *Arzneimittelforschung*, 21:1234-1243 (1971), Glen, J. B., *Br J Anaesth*, 52:731-742 (1980), and Zhou, Anesth Analg, 102:129-134 (2006)). The relatively large safety margin afforded by etomidate presumably reflects its lesser effect on cardiovascular and respiratory function. The hemodynamic stability afforded by etomidate is due, at least in part, to its lack of depressant effect on sympathetic outflow and autonomic reflexes (Ebert, T. J., et al., *Anesthesiology* 76:725-733 (1992)). Conversely, propofol and thiopental reduce sympathetic outflow, blunt autonomic reflexes and directly impair myocardial contractility (Mazerolles, M., *Fundam Clin Pharmacol*, 10:298-303 (1996)). These actions produce cardiovascular depression even in healthy patients. Because of (R)-etomidate's lesser effects on cardiovascular and respiratory function, it has emerged as an anesthetic agent of choice by anesthesiologists, intensivists, and emergency room physicians for use in sick, elderly, or traumatized patients. However, this enthusiasm is tempered and its clinical use limited by its remarkably potent and prolonged inhibition of adrenocortical steroid synthesis.

Inhibition of steroid synthesis is a potentially deadly side effect of prolonged (R)-etomidate administration, particularly in those patients who would otherwise benefit most from its favorable cardiovascular and respiratory properties: the critically ill. This inhibition is extremely potent, occurring at (R)-etomidate concentrations far below those used to produce sedation or anesthesia. At the doses necessary to produce general anesthesia, (R)-etomidate causes adrenal insufficiency that can persist for more than 4 days after discontinuing a prolonged infusion (Wagner, R. L., and White, P. F., *Anesthesiology*, 61:647-651 (1984)), resulting in significantly increased mortality in critically ill patients (Watt, I., and Ledingham, I. M., *Anaesthesia*, 39:973-981 (1984) and Ledingham, I. M., and Watt, I., *Lancet*, 1:1270 (1983)). Apparently, mortality can be reduced by empirically administering exogenous steroids; however, this approach is suboptimal as the dosing, timing, and duration of steroid therapy in any given patient would be speculative. Furthermore, the administration of exogenous steroids itself can produce serious complications including impaired glucose homeostasis and wound healing, immunosuppression, and fluid retention. Because of (R)-etomidate's profound effect on adrenocortical function, a specific warning against its administration by prolonged infusion has been added to its package insert and the use of (R)-etomidate for prolonged sedation or anesthesia has been abandoned.

The clinical significance of adrenocortical suppression following a single I.V. bolus is controversial. See Morris, C., and McAllister, C., *Anaesthesia*, 60:737-740 (2005); Jackson, W. L., Jr., *Chest*, 127:1031-1038 (2005); Murray, H., and Marik, P. E., *Chest*, 127:707-709 (2005); Zed, P. J., et al., *Chem.*, 8:347-350 (2006); and Bloomfield, R., and Noble, D. W., *Crit Care*, 10:161 (2006). It has historically been assumed that adrenal suppression following a single bolus is brief (<8 hrs) and clinically unimportant. However, this assumption is mainly based on small studies of patients undergoing elective surgery who were not critically ill. See Wagner, R. L., and White, P. F., *Anesthesiology*, 61:647-651 (1984); Wagner, R. L., et al., *N Engl J Med*, 310:1415-1421 (1984); Fragen, R. J., et al., *Anesthesiology* 61:652-656 (1984); and Duthie, D. J., et al., *Br J Anaesth*, 57:156-159 (1985). A number of recent studies and reports of critically ill patients indicate that adrenal suppression following even a single bolus induction dose of (R)-etomidate can last for 24 hours or longer and some suggest that it increases the risk of death, particularly in the setting of sepsis. See Absalom A., et al., *Anaesthesia*, 54:861-867 (1999); Malerba, G., et al., *Intensive Care Med*, 31:388-392 (2005); den Brinker, M., et al., *Intensive Care Med* (2007); den Brinker, M., et al., *J Clin Endocrinol Metab*, 90:5110-5117 (2005); Lundy, J. B., et al., *J Intensive Care Med*, 22:111-117 (2007); Lipiner-Friedman, D., et al., *Crit Care Med*, 35:1012-1018 (2007); Vinclair, M., et al., *Intensive Care Med.*, (2007); and Cotton, B. A., et al., *Arch Surg*, 143:62-67 (2008).

(R)-etomidate inhibits adrenocortical steroid synthesis primarily by inhibiting 11β-hydroxylase, a critical enzyme in the synthetic pathway leading to cortisol, corticosterone, and aldosterone production (see de Jong, F. H., et al., *J Clin Endocrinol Metab*, 59:1143-1147 (1984)). (R)-etomidate's half-maximal inhibitory concentration (IC50) has been reported to be 0.5-30 nM (see Lamberts, S. W., et al., *J Pharmacol Exp Ther*, 240:259-264 (1987)), a concentration range that is orders of magnitude lower than its anesthetizing concentration. When (R)-etomidate's extremely high 11β-hydroxylase inhibitory potency is considered along with its lengthy (several hours) elimination half-life (see Van Hamme, M. J., et al., *Anesthesiology*, 49:274-277 (1978)), we suggest that a logical explanation emerges for the long duration of adrenocortical suppression following (R)-etomidate administration: After administering an anesthetic dose, many elimination half-lives must pass before (R)-etomidate's serum concentration is sufficiently reduced by metabolism so that 11β-hydroxylase activity is no longer inhibited. This led to the prediction that the duration of adrenocortical suppression might be reduced by designing analogues of (R)-etomidate that are rapidly metabolized. Such rapidly metabolized analogues might also be predicted to have ultra-short durations of anesthetic action. This is another highly desirable anesthetic property because it allows more precise titration of anesthetic depth during surgery and faster emergence from anesthesia at the end of surgery.

There is a great need for safer general anesthetics, particularly for use in the critically ill. (R)-etomidate possesses many properties that make it an ideal general anesthetic agent, but its ability to potently suppress adrenocortical steroid synthesis severely limits its clinical utility and safety.

As discussed above, there is a need in the art to develop analogues of (R)-etomidate that retain it's many beneficial properties (e.g. rapid onset of action, little effect on blood pressure, high therapeutic index), but do not cause potentially dangerous inhibition of adrenocortical function. Such analogues will permit anesthesia to be administered more safely to patients who are critically ill. This invention answers that need.

SUMMARY OF THE INVENTION

The invention is directed to compounds according to formula (I):

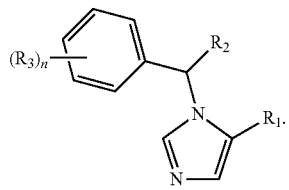

Compounds of formula (I) have improved pharmacokinetic and pharmacodynamic properties over (R)-etomidate that allow for equivalent or improved anesthetic properties along with a reduction in undesirable side effects. Compounds of formula (I) are analogues of etomidate that retain (R)-etomidate's beneficial anesthetic properties, but do not cause clinically significant inhibition of adrenocortical function.

In formula (I), $R_1$ is $L_1C(O)OT$ or $L_1C(O)OL_2C(O)OT$. $R_2$ is a substitute or unsubstituted $C_1$-$C_{10}$ alkyl, $C_2$-$C_{10}$ alkenyl, or $C_2$-$C_{10}$ alkynyl, or $R_1$. $R_3$ are each independently halogen or $R_2$. n is an integer from 0 to 5. $L_1$ and $L_2$ are each independently a bond, or a substituted or unsubstituted $C_1$-$C_{10}$ alkylene, $C_2$-$C_{10}$ alkenylene, or $C_2$-$C_{10}$ alkynylene. T is H, a substituted or unsubstituted $C_1$-$C_{10}$ alkyl, $C_2$-$C_{10}$ alkenyl, or $C_2$-$C_{10}$ alkynyl, nitrophenol, or cyclopropyl. The compounds of formula (I) include pharmaceutically acceptable salts, stereoisomer mixtures, and enantiomers thereof. Compounds of formula (I) are the subject of this invention provided that when $R_1$ is $L_1C(O)OT$, $R_2$ is $CH_3$, $R_3$ is fluorine, n is 1, and T is $CH_2CH_3$, $L_1$ is not a bond.

Another aspect of the invention is directed to a pharmaceutical anesthetic composition comprising an effective amount of a compound according to formula (I) and a pharmaceutically acceptable carrier.

Yet another aspect of the invention is directed to a method for providing anesthesia in a mammal or including administering to the mammal an effective anesthetic compound of formula (I) or a pharmaceutical composition.

Another aspect of the present invention is use of the compounds of formula (I) substantially as described herein as a formulation for, or in the manufacture of a formulation for providing anesthesia in a subject in need thereof.

BRIEF DESCRIPTION OF THE DRAWINGS

FIG. 7A shows the propofol, (R)-etomidate, and MOC-(R)-etomidate dose-response relationships for anesthesia (measured as LORR) in rats. FIG. 7B demonstrates that the duration of anesthesia increased approximately linearly with the logarithm of the anesthetic dose and that this duration is significantly shorter for MOC-(R)-etomidate than either (R)-etomidate or propofol.

DETAILED DESCRIPTION OF THE INVENTION

Figure 1:
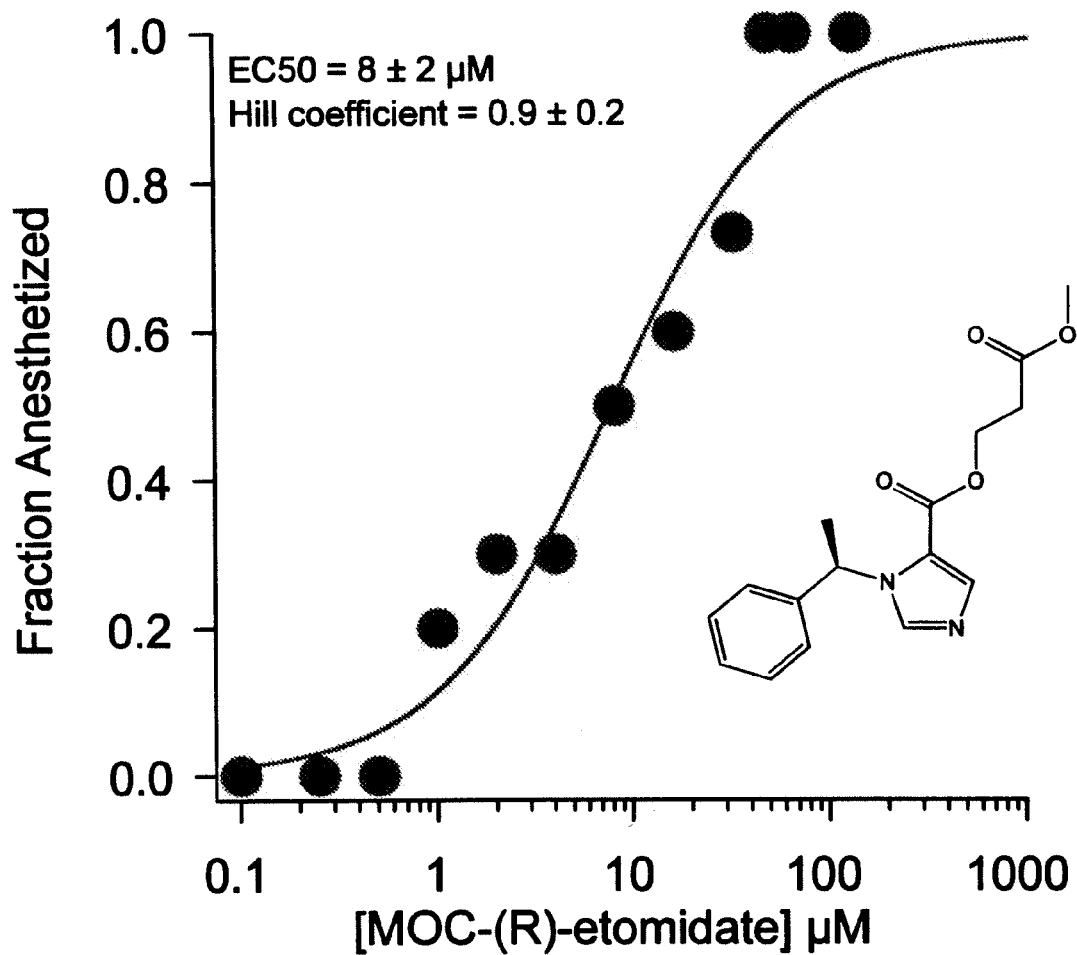
FIG. 1 is a graph showing the MOC-(R)-etomidate concentration-response relationship for anesthesia (measured as loss of righting reflexes; LORR) in tadpoles. A total of 100 tadpoles were used to define this concentration-response curve. The anesthetic EC50 was 8±2 μM. This demonstrates that MOC-(R)-etomidate is a potent general anesthetic. For comparison, (R)-etomidate's EC50 is 2 μM (see Husain S S et al. *J Med Chem* (2003).

This invention relates to safer analogues of (R)-etomidate that retain its beneficial characteristics (e.g. potent anesthetic, rapid onset of anesthesia, little effect on blood pressures), but whose impact on adrenocortical steroid synthesis and/or duration of anesthetic action is substantially reduced. Certain embodiments include analogues of etomidate (either the R- or S-enantiomer) that are so rapidly metabolized to a poorly active metabolite (i.e. a metabolite that does not significantly inhibit 11β-hydroxylase, enhance GABA$_A$ receptor function, and/or produce anesthesia) that suppression of adrenocortical function and/or anesthetic action terminates shortly after discontinuing anesthetic administration.

The compounds of the invention can be understood as analogues of etomidate (either R- or S-enantiomer) augmented with one or more additional metabolically-labile ester moieties attached to various positions of the core molecule directly or via various linker groups (for example, —CH$_2$CH$_2$—). Distal to the ester moieties, there may be a "tail" group (for example, —CH$_3$). The various embodiments of this invention are discussed below.

The invention is directed to compounds according to formula (I):

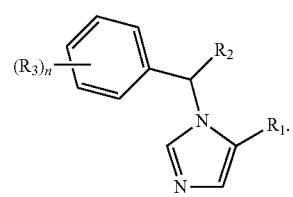

I

R$_1$ is L$_1$C(O)OT or L$_1$C(O)OL$_2$C(O)OT. In a preferred embodiment, R$_1$ is L$_1$C(O)OL$_2$C(O)OT.

R$_2$ is a substituted or unsubstituted C$_1$-C$_{10}$ alkyl, C$_2$-C$_{10}$ alkenyl, or C$_2$-C$_{10}$ alkynyl, or R$_1$. Preferably, R$_2$ is an alkyl, such as CH$_3$ or an ester of R$_1$, such as CH$_2$CH$_2$C(O)OCH$_3$. In a most preferred embodiment, R$_2$ is CH$_3$.

R$_3$ are each independently halogen or R$_2$. Preferred halogens include fluorine and chlorine. The variable n is an integer from 0 to 5. In a preferred embodiment, n ranges from 0-3, and is most preferably 0.

The linkers L$_1$ and L$_2$ are each independently a bond, a substituted or unsubstituted C$_1$-C$_{10}$ alkylene, C$_2$-C$_{10}$ alkenylene, or C$_2$-C$_{10}$ alkynylene group. The backbone of alkylene may contain one or more heteroatoms, such as O, N, or S. Preferably, L$_1$ and L$_2$ are each independently a bond or a linear C$_1$-C$_4$ alkylene group. Most preferably, L$_1$ is a bond or CH$_2$CH$_2$, and L$_2$ is CH$_2$CH$_2$, CH$_2$(CH$_2$)$_4$CH$_2$, or CH$_2$CH$_2$O(CH$_2$)$_3$. In a most preferred embodiment, L$_2$ is CH$_2$CH$_2$.

The tail T may be H, a substituted or unsubstituted C$_1$-C$_{10}$ alkyl, C$_2$-C$_{10}$ alkenyl, or C$_2$-C$_{10}$ alkynyl. The backbone of alkyl may contain one or more heteroatoms, such as O, N, or S. The tail may also be cyclopropyl, nitrophenol, or any other suitable electron withdrawing group. Preferably, T is a C$_1$-C$_4$ alkyl group. Most preferably T is CH$_3$, CH$_2$CH$_3$, CH$_2$CH$_2$CH$_2$CH$_3$, or CH$_2$CH$_2$OCH$_3$. In a most preferred embodiment, T is CH$_3$. In another most preferred embodiment, T is nitrophenol.

The compounds of formula (I) include pharmaceutically acceptable salts, stereoisomer mixtures, and enantiomers thereof. The compounds of the invention also include physiologically acceptable salts of the compounds of formula (I). Preferred physiologically acceptable salts are acid-addition salts known to those of skill in the art. Common physiologically acceptable acid-addition salts include but are not limited to, hydrochloric acid salts, oxalate salts, and tartrate salts.

In a preferred embodiment of the compound, R$_1$ is L$_1$C(O)OL$_2$C(O)OT, R$_2$ is CH$_3$, n is 0, L$_1$ is a bond, L$_2$ is CH$_2$CH$_2$, and T is CH$_3$.

In another embodiment of the compound, R$_1$ is L$_1$C(O)OL$_2$C(O)OT, R$_2$ is CH$_3$, n is 0, L$_1$ is a bond, L$_2$ is CH$_2$(CH$_2$)$_4$CH$_2$, and T is CH$_2$CH$_2$CH$_2$CH$_3$.

In yet another embodiment of the compound, $R_1$ is $L_1C(O)OL_2C(O)OT$, $R_2$ is $CH_3$, n is 0, $L_1$ is a bond, $L_2$ is $CH_2CH_2O(CH_2)_3$, and T is $CH_2CH_2OCH_3$.

In certain embodiments of the compound, $R_1$ is $L_1C(O)OL_2C(O)OT$, $R_2$ is $CH_3$, each $R_3$ independently is halogen, n is 1-5, $L_1$ is a bond, $L_2$ is $CH_2CH_2$, and T is $CH_3$.

In other embodiments of the compound, $R_1$ is $L_1C(O)OL_2C(O)OT$, $R_2$ is $CH_3$, each $R_3$ is fluorine, n is 1-5, $L_1$ is a bond, $L_2$ is $CH_2CH_2$, and T is $CH_3$.

In still yet other embodiments of the compound, $R_1$ is $L_1C(O)OL_2C(O)OT$, $R_2$ is $CH_3$, each $R_3$ is fluorine, $L_1$ is a bond, $L_2$ is $CH_2CH_2$, and T is $CH_3$.

In other embodiments of the compound, $R_1$ is $L_1C(O)OT$, $R_2$ is $CH_3$, at least one $R_3$ is $CH_2CH_2C(O)OCH_3$, $L_1$ is a bond, and T is $CH_2CH_3$.

In further embodiments of the compound, $R_1$ is $L_1C(O)OL_2C(O)OT$, $R_2$ is $CH_3$, at least one $R_3$ is $CH_2CH_2C(O)OCH_3$, $L_1$ is a bond, $L_2$ is $CH_2CH_2$, and T is $CH_3$.

In a preferred embodiment of the compound, $R_1$ is $L_1C(O)OT$, $R_2$ is $CH_2CH_2C(O)OCH_3$, n is 0, $L_1$ is a bond, and T is $CH_2CH_3$.

In another preferred embodiment of the compound, $R_1$ is $L_1C(O)OT$, $R_2$ is $CH_3$, n is 0, $L_1$ is $CH_2CH_2$, and T is $CH_2CH_3$.

The carbon atom bridging the 6-membered ring and the 5-membered ring is a chiral center. Therefore, the compound may be in the form of a pure enantiomer. In a preferred embodiment, the enantiomer is the R enantiomer.

Compounds of formula (I) preferably have the same stereochemistry as (R)-etomidate. $R_2$, $R_3$, $L_1$, $L_2$, and T can be branched hydrocarbon chains, however, not to the extent that steric hindrance or conjugation interferes with the desired activity.

In a certain embodiments, the compound includes two or more ester groups. Suitable ester-containing groups (e.g. linker-ester-tail or ester-tail) can be added to the bridging carbon or at various positions of the phenyl ring or the core molecule.

Rapidly metabolized etomidate analogues with new ester moieties on (R)-etomidate that are sterically unhindered and/or electronically isolated from the pi electron systems in the imidazole and phenyl rings are preferred. Such ester moieties, like those in other ultra-short acting drugs like remifentanil and esmolol, are believed to be highly susceptible to hydrolysis by esterases. See U.S. Pat. Nos. 3,354,173; 5,466,700; 5,019,583; and U.S. Patent Publication No. US 2003/0055023.

The $R_2$, T, $L_1$, and $L_2$ substituents may each independently be substituted with one or more electron withdrawing groups. In a certain embodiments, the electron withdrawing group is a halogen, nitrophenol, or cyclopropyl. Other electron withdrawing groups such as hydroxy groups, amino groups, nitro groups, nitrile groups, sulfonate groups, carboxylate groups, halide groups, mercaptan groups, and unsaturated alkyl groups, may also be used. The presence of electron withdrawing groups serves to increase the partial positive charge on the ester carbonyl atom, thereby increasing susceptibility to nucleophilic attack by esterases and further enhancing rapid hydrolysis by esterases.

Another aspect of the invention is directed to a pharmaceutical composition comprising a compound according to formula (I) and a pharmaceutically acceptable carrier.

Yet another aspect of the invention is directed to a method for providing anesthesia in a mammal including administering to the mammal a pharmaceutical composition substantially the same as described above.

In certain embodiments, the method includes administering an effective dose of the compound. The effective dose comprises 0.01 to 100 mg/kg of the compound.

In a preferred embodiment, the method includes administering an injection of a single effective dose of the compound which may or may not be followed by a continuous infusion of the compound.

In certain embodiments, the method includes administering a continuous infusion of an effective dose of the compound of formula (I).

In certain embodiments, the method also includes administering to the mammal an effective amount of a therapeutic agent selected from another sedative hypnotic agent, an analgesic agent, and a paralytic agent. Non-limiting examples of sedative hypnotic agents include benzodiazepines, barbiturates, ketamine, propofol, isoflurane, and desflurane. Non-limiting examples of analgesic agents include non-steroidal anti-inflammatory drugs (NSAIDs), paracetamol/acetaminophen, COX-2 inhibitors, and opioids. Non-limiting examples of paralytic agents include rapacuronium, mivacurium, succinylcholine, vecuronium, and cisatracurium.

The compounds of the invention have demonstrated anesthetic and enhanced $GABA_A$ receptor activities. Concentrations tested in in vitro assays ranged from $4.34 \times 10^{-5}$ to $3.39 \times 10^{-8}$ g/mL and 0.01 to 0.02 g/kg in in vivo assays. Compounds of the invention uniformly demonstrated potent in vitro and in vivo anesthetic and enhanced $GABA_A$ receptor effects. These results indicate that compounds of the invention are highly active agents with potent in vitro and in vivo activities. Importantly, the compounds have reduced inhibitory activity with respect to in vitro and in vivo adrenocortical steroid synthesis and/or short durations of anesthetic action.

The compounds described above can either be administered alone in the form of mixtures with one another, or in combination with acceptable pharmaceutical carriers. The invention, thus, also relates to pharmaceutical compositions which comprise an effective amount of at least one compound of the invention with or without a pharmaceutically or physiologically acceptable carrier. If appropriate, the compound may be administered in the form of a physiologically acceptable salt, for example, an acid-addition salt.

The invention also encompasses a method of treating animals or humans. This method comprises administering to the animal or person an effective amount of at least one of the compounds of the invention, or a physiologically acceptable salt thereof, with, or without a pharmaceutically acceptable carrier. Intravenous administration is preferred. See U.S. Pat. No. 4,289,783, which is hereby incorporated by reference in its entirety.

The invention is a potent sedative hypnotic that is rapidly metabolized and may be used to produce and/or maintain anesthesia, sedation, or otherwise lower central nervous system excitability. It exhibits one or more of the following beneficial properties as compared to alternative agents: higher potency, shorter duration of therapeutic action, shorter duration of side effects, reduced adrenocortical suppression, higher therapeutic index, lower toxicity, reduced cardiovascular depression, and greater ease of titration to desired effect. The invention may be administered as a single IV bolus or a continuous IV infusion. Other route of delivery may include oral, rectal, transmucosal, subcutaneous, or inhaled.

The compounds of the invention may be prepared by methods disclosed in U.S. Pat. No. 3,354,173, which is hereby incorporated by reference in its entirety. Suitable modification to starting materials by methods well known in the art may be employed. The compounds of the invention may also be prepared according to a general synthetic procedure can be described as follows. First, the ester linkage of etomidate or an etomidate analog is hydrolyzed to produce imidazole-5-carboxylic acid. Next, the carboxylic acid is coupled with a suitable ester-containing group (e.g. linker-ester-tail). Coupling can be achieved via carbodiimide chemistries or other methods known in the art. It is preferred when beginning with (R)-etomidate or its analog that the stereochemistry is preserved.

The examples below demonstrate the general synthetic procedure, as well as the specific preparation, for compounds according to this invention. The following examples demonstrate the preparation of compounds according to this invention. The examples are illustrative, and are not intended to limit, in any manner, the claimed invention.

EXAMPLES

Example 1

Synthesis of (R)-1-(1-phenylethyl)-1H-Imidazole-5-carboxylic Acid (1)

A solution of R-ethyl-1-(1-phenylethyl)-1H-imidazole-5-carboxylate.HCl (R-etomidate.HCl), 281 m g, 1 mmol) in methanol (5 ml) and 10% aqueous NaOH (1.7 ml) was refluxed for 30 min. After cooling, the solution was neutralized with 12.1 M HCl (0.351 ml). The mixture was dried by rotary evaporation, the residue suspended in methanol-dichloromethane 1:4 v/v and sodium chloride filtered off. 1-(1-phenylethyl)-1H-imidazole-5-carboxylic acid 1 was obtained by chromatography on silica gel column, equilibrated with methanol-dichloromethane 1:4 V/V. $^1$HNMR spectrum: (CD$_3$OD) δ 9.30(d, 1H, imidazole CH), 8.23 (d, 1H, imidazole CH), 7.37 (m, 5H, phenyl), 6.64 (q, 1H, methine), 1.97 (d, 3H, methyl). See Scheme 1.

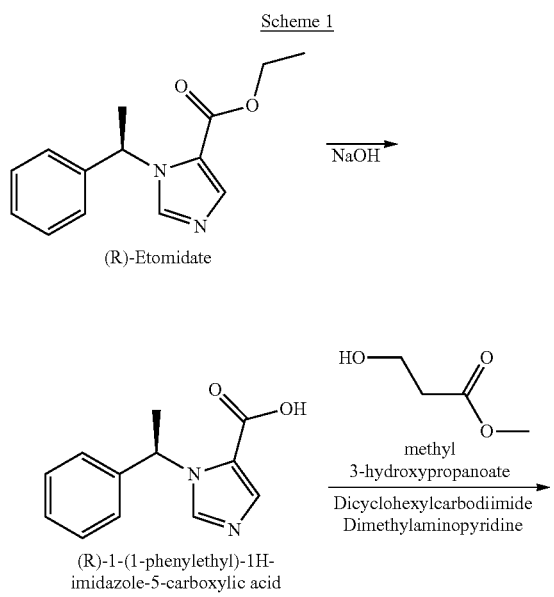

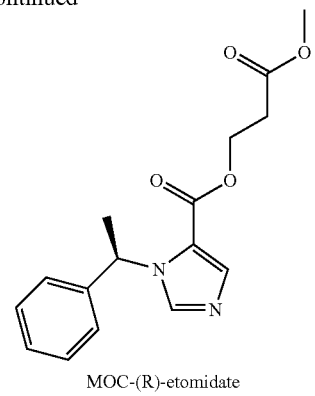

MOC-(R)-etomidate

Example 2

Synthesis of Methyl-3-hydroxypropanoate (2)

The compound was prepared essentially as described by Bartlett and Rylander (see Bartlett, P. D. and Rylander, P. N., *J. Amer. Chem. Soc.*, 73: 4273-4274 (1951), which is hereby incorporated by reference in its entirety). β-Propiolactone (4.36 g, 60.5 mmol) was added drop-wise to a stirred solution of sodium methoxide (121 mg, 2.24 mmol) in anhydrous methanol (15 ml) at −78° C. The mixture was neutralized by adding equivalent amount of HCl (2.24 ml 1M HCl). The mixture was filtered, rotary evaporated to remove methanol and the oily residue distilled at reduced pressure to obtain methyl-3-hydroxypropanoate 2 (2.7 g, 43%). $^1$HNMR spectrum: (CDCl$_3$) δ 3.88 (t, 2H, methylene), 3.73 (s, 3H, methyl), 2.59 (d, 2H, methylene).

Example 3

Synthesis of (R)-3-Methoxy-3-oxopropyl1-(1-phenylethyl)-1H-imidazole-5-carboxylate (MOC-(R)-Etomidate, 3)

To a mixture of (R)-1-(1-phenylethyl)-1H-imidazole-5-carboxylic 1 (1 mmol) and methyl-3-hydroxypropanoate (115 mg, 1.1 mmol) in anhydrous dichloromethane (3.5 ml) was added dicyclohexylcarbodiimide (139 mg, 1.1 mmol) and p-dimethylaminopyridine (134 mg, 1.1 mmol). The solution was stirred at room temperature for 48 h. The precipitate was filtered off and the clear solution applied to a silica gel column, equilibrated with dichloromethane. Elution with 10% ether in dichloromethane gave the product which was further purified by preparative thin layer chromatography with hexane-ethyl acetate 1:1 v/v on 1 mm thick silica gel plate. The oily product was treated with HCl in anhydrous ethyl acetate to obtain white, crystalline 3-methoxy-3-oxopropyl1-(1-phenylethyl)-1H-imidazole-5-carboxylate.HCl (MOC-(R)-etomidate .hydrochloride) (200 mg, 59%).
$^1$HNMR spectrum: (CDCl$_3$) δ 8.92 (d, 1H, imidazole CH), 7.76 (d, 1H, imidazole CH), 7.36 (m, 5H, phenyl), 6.49 (q, 1H, methine), 4.60 (m, 2H, methylene), 3.73 (s, 3H, methyl), 2.76 (t, 2H, methylene), 2.01 (d, 3H, methyl).

Example 4

MOC-(R)-Etomidate is a Potent General Anesthetic in Tadpoles

The tadpole loss of righting reflex assay was used to test for anesthetic activity. Groups of 5 early prelimb-bud stage *Xeno-* pus laevis tadpoles were placed in 100 ml of oxygenated water buffered with 2.5 mM Tris HCl buffer (pH=7) and containing a concentration of MOC-(R)-etomidate ranging from 0.1-128 µM. See Scheme 1, above, for structure of MOC-(R)-etomidate. Tadpoles were tipped manually every 5 min with a flame polished pipette. Tadpoles were deemed to be anesthetized if they failed to right themselves within 5 sec. At all concentrations, this loss of righting reflex response stabilized within 30 min of MOC-(R)-etomidate exposure. No evidence of toxicity was observed; all anesthetized tadpoles recovered their righting reflexes when returned to fresh oxygenated water.

FIG. 1 shows the MOC-(R)-etomidate concentration-response curve for anesthesia. The fraction of tadpoles anesthetized in each group increased with MOC-(R)-etomidate concentration and at the highest MOC-(R)-etomidate concentrations (48-128 µM), all tadpoles were anesthetized. From this data, MOC-(R)-etomidate's anesthetic EC50 (i.e. the concentration at which 50% of tadpoles were anesthetized) was determined to be 8±2 µM.

Example 5

MOC-(R)-Etomidate Significantly Enhances $GABA_A$ Receptor Function

MOC-(R)-etomidate was designed to produce anesthesia by the same molecular mechanism as (R)-etomidate: by enhancing $GABA_A$ receptor function. Human $GABA_A$ receptors composed of $\alpha_1\beta_2\gamma_{2L}$ subunits were expressed in *Xenopus laevis* oocytes and used to compare the effects of MOC-(R)-etomidate and (R)-etomidate on $GABA_A$ receptor mediated currents using the two-microelectrode voltage clamp technique. This subunit combination was chosen because it forms the most prevalent $GABA_A$ receptor subtype in the brain and is known to be etomidate-sensitive.

Figure 2:
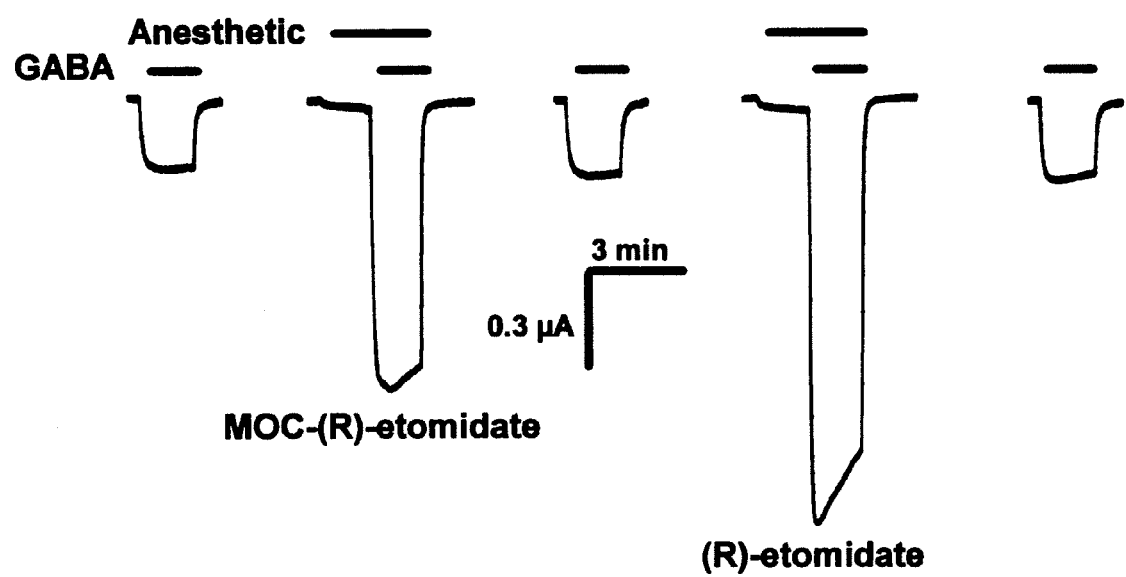
FIG. 2 shows electrophysiological traces demonstrating enhancement of currents mediated by human $\alpha_1\beta_2\gamma_{2L}$ $GABA_A$ receptors expressed in *Xenopus* oocytes by either MOC-(R)-etomidate or (R)-etomidate at their respective anesthetic concentrations. The first, third, and fifth traces are controls. The second and forth traces show the similar enhancing effects of 8 μM MOC-(R)-etomidate and 2 μM (R)-etomidate, respectively. This demonstrates that like (R)-etomidate, MOC-(R)-etomidate enhances submaximal GABA-evoked GABA$_A$ receptor currents.

In each oocyte, the GABA concentration that evokes a current response whose peak amplitude was 5-10% of that evoked by 1 mM GABA (a receptor-saturating GABA concentration) was determined. This submaximal concentration is termed the $EC_{5-10}$ GABA concentration. To assess and compare the effects of MOC-(R)-etomidate and (R)-etomidate on GABAergic currents, the "control" current evoked by $EC_{5-10}$ GABA alone was measured. After a 5 min recovery period, the "test" peak current was measured by exposing oocytes to anesthetic for 90 sec and then both anesthetic and $EC_{5-10}$ GABA for 90 sec. After another 5 min recovery period, the control experiment was repeated to assure reversibility. FIG. 2 shows representative control and test traces obtained in the absence and presence of anesthetic, respectively in the same oocyte. It was found that, at its anesthetic EC50 (i.e. 8 µM), MOC-(R)-etomidate enhanced the amplitudes of GABA-evoked currents by 450±130% (n=6 oocytes). This is similar to the enhancement produced by (R)-etomidate (660±240%) at its anesthetic EC50 (i.e. 2 µM) in the same set of oocytes. Direct activation was also observed as both MOC-(R)-etomidate and (R)-etomidate evoked small currents even before the application of GABA.

Figure 3:
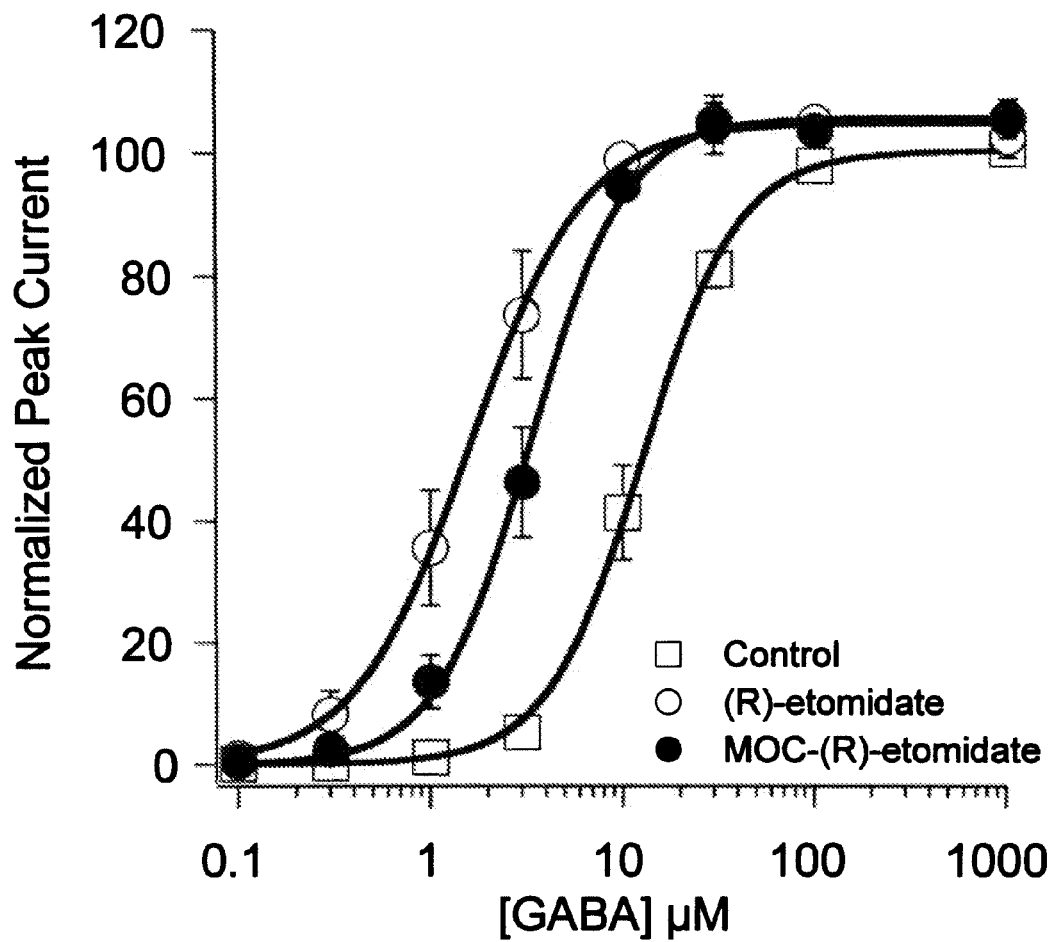
FIG. 3 shows a graph of GABA concentration-response curves in the absence or presence of either 8 μM MOC-(R)-etomidate or 2 μM (R)-etomidate. This demonstrates that like (R)-etomidate, MOC-(R)-etomidate shifts the GABA$_A$ receptor's GABA concentration-response curve leftward. Each data point represents the mean of measurements from three different oocytes. The error bars indicate the S.D. of the mean.

Next, the abilities of MOC-(R)-etomidate and (R)-etomidate to shift the GABA concentration-response curve leftward were examined (See FIG. 3). In these experiments, the peak current response obtained at each GABA concentration was normalized to the maximal response elicited by 1 mM GABA. At their anesthetic EC50 concentrations, MOC-(R)-etomidate and (R)-etomidate enhanced currents evoked by low GABA concentrations, but had relatively little effect on currents evoked by high GABA concentrations. This shifted the GABA concentration-response curves leftward, reducing the GABA EC50 (i.e. the concentration of GABA that elicits 50% of the maximal response) from 12.7±0.4 µM in the absence of anesthetic to 3.3±0.1 µM with MOC-(R)-etomidate and 1.6±0.1 µM with (R)-etomidate, respectively. The Hill coefficients ranged from 1.5-1.8.

Example 6

In Vitro Metabolism of MOC-(R)-Etomidate is >100-Fold Faster than (R)-Etomidate

The in-vitro rate of metabolism (in pooled human S9 liver fraction) of MOC-(R)-etomidate was compared to that of (R)-etomidate. S9 liver fraction was chosen because it is rich in a wide variety of drug-metabolizing enzymes (including esterases) and is commonly used to assay drugs for metabolic stability. As the liver is likely to be a relevant organ for in-vivo MOC-(R)-etomidate metabolism, it also represents a relevant source of enzymes for in-vitro metabolic studies.

10 µM each of MOC-(R)-etomidate or (R)-etomidate was incubated at 37° with 0.3 mg/ml of pooled human S9 liver fraction containing 1 mM NADPH. At various time points (0, 5, 10, 20, and 40 min), a 100 µL aliquot of the reaction mixture was removed and its metabolism was stopped by adding 200 µL acetonitrile. The aliquot was centrifuged and the concentration of (unmetabolized) anesthetic in the supernatant was quantified using HPLC with mass spectrometric detection.

Figure 4:
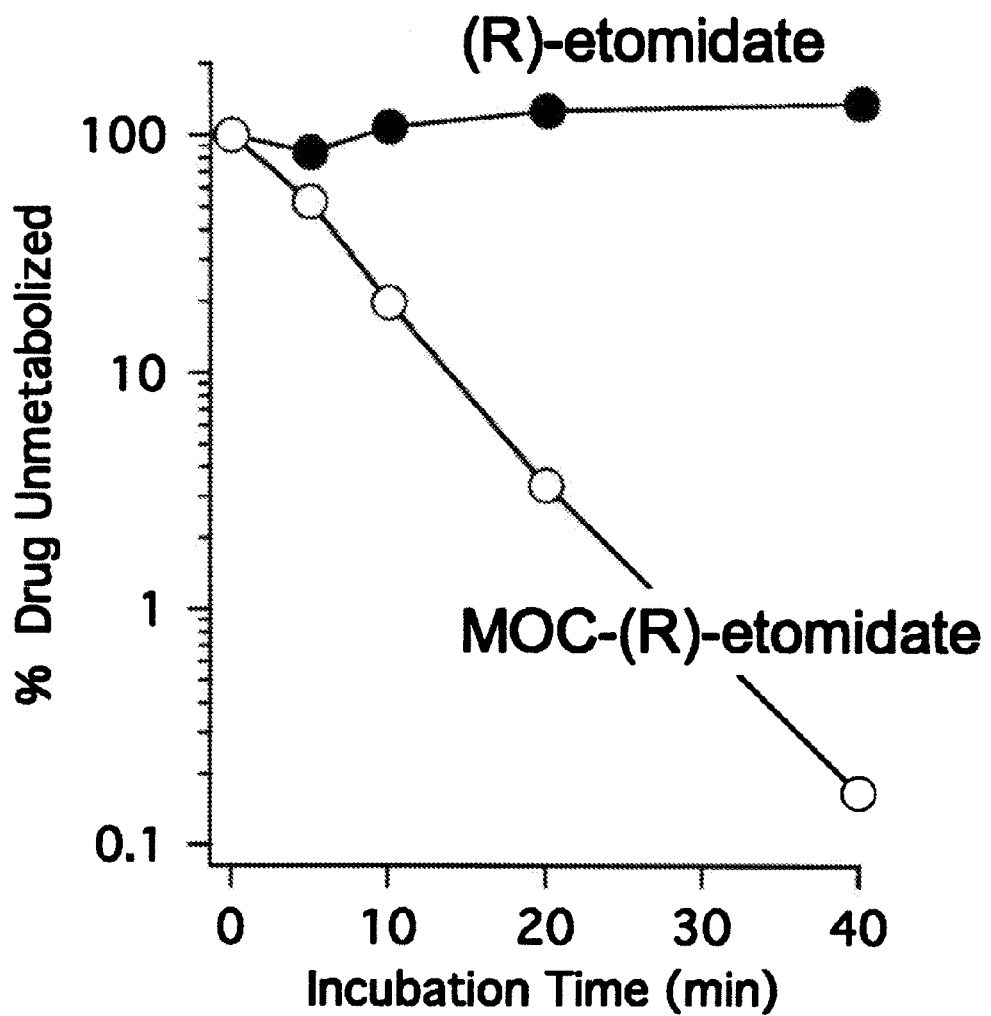
FIG. 4 shows a graph of the percentage of unmetabolized (R)-etomidate or unmetabolized MOC-(R)-etomidate as a function of incubation time when incubated with human S9 liver fraction (+NADPH) at 37° C. By 40 min., more than 99% of MOC-(R)-etomidate was metabolized whereas (R)-etomidate was not measurably metabolized on this time scale. This demonstrates that MOC-(R)-etomidate is metabolized by liver enzymes at least 100-fold faster than (R)-etomidate.

FIG. 4 plots the percentage of unmetabolized anesthetic remaining as a function of incubation time in S9 liver fraction on a semi logarithmic scale. Even after 40 min, no metabolism of (R)-etomidate was detected, indicating that its in-vitro metabolic half-lives was much longer than 40 min. In sharp contrast, MOC-(R)-etomidate was rapidly metabolized in the human S9 liver fraction. The concentration of MOC-(R)-etomidate decreased as a first-order process reaching <1% of the original concentration (i.e. <0.1 µM) by 40 min. The metabolic half-life of MOC-(R)-etomidate was calculated to be 4.2 min. In these studies, buspirone was used as an internal standard to confirm metabolic activity in the liver fraction. Its metabolic half-life was 15.4 min.

The structure of the metabolite formed after 40 min of incubation in pooled human liver S9 fraction (+ nicotinamide adenine dinucleotide phosphate) was analyzed using high performance liquid chromatography/tandem mass spectrometry. The ion chromatogram detected the presence of only one metabolite. It had a molecular weight of 288, which is consistent with the carboxylic acid formed upon hydrolysis of MOC-(R)-etomidate's distal ester moiety. Based on these results, we conclude that rapid metabolism of MOC-(R)-etomidate occurs exclusively via the designed pathway shown in Scheme 2 in which the distal ester moiety of MOC-(R)-etomidate is hydrolyzed to form the corresponding carboxylic acid along with methanol as the leaving group.

Scheme 2

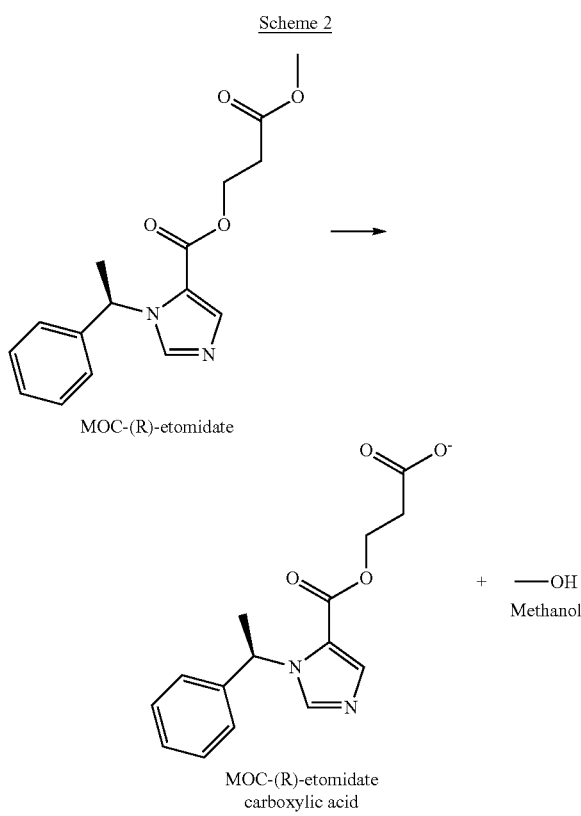

MOC-(R)-etomidate

MOC-(R)-etomidate carboxylic acid

+ —OH Methanol

Example 7

MOC-(R)-Etomidate's Metabolite Has Little or No Anesthetic Action

MOC-(R)-etomidate's metabolite (i.e. MOC-(R)-etomidate carboxylic acid) was produced by hydrolyzing MOC-(R)-etomidate in phosphate buffered solution containing ~1 unit/ml of esterase from porcine liver. During hydrolysis, the pH was maintained at 8.4 by adding NaOH. The reaction product was then purified on a TLC plate. NMR spectroscopy confirmed that >99% of the MOC-(R)-etomidate had been hydrolyzed to the expected carboxylic acid metabolite.

The metabolite was tested for anesthetic activity using the tadpole loss of righting reflex assay. In this assay, 5 tadpoles were added to 20 ml beaker containing the metabolite at concentrations of 1000 µM. Even after 60 min, none of the tadpoles lost their righting reflex indicating that the metabolite has no significant anesthetic activity.

Example 8

Figure 5:
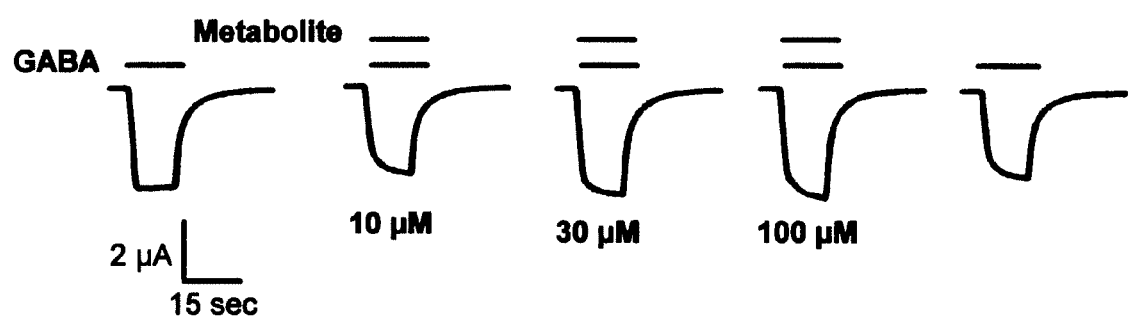
FIG. 5 shows electrophysiological traces demonstrating the lack of enhancement of currents mediated by human $\alpha_1\beta_2\gamma_{2L}$ GABA$_A$ receptors expressed in Xenopus oocytes by MOC-(R)-etomidate's carboxylic acid metabolite. The first and last traces are controls (i.e. no metabolite). The second, third, and fourth traces show the lack of effect of 10, 30, and 100 μM metabolite.

MOC-(R)-Etomidate's Metabolite Has Little or No Effect on $GABA_A$ Receptor Function The $GABA_A$ receptor enhancing activity of MOC-(R)-etomidate's metabolite was assessed using the two-microelectrode voltage clamp technique. FIG. 5 shows that even at concentrations up to 100 µM, MOC-(R)-etomidate's metabolite had no significant effect on $GABA_A$ receptor currents.

Example 9

MOC-(R)-Etomidate's Metabolite Has Little or No Effect on In Vitro Steroid Synthesis The ability of MOC-(R)-etomidate's metabolite to inhibit in vitro steroid synthesis was assessed using the human adrenocortical carcinoma cell line H295R (NCI-H295R; ATCC #CRL-2128). H295R cells express most of the key enzymes necessary for steroidogenesis, including all of those required for cortisol biosynthesis (e.g. 11β-hydroxylase). When stimulated with forskolin, these cells produce cortisol and secrete it into the medium where it can be readily measured. Inhibition of 11β-hydroxylase blocks cortisol synthesis, reducing the concentration of cortisol in the assay medium.

H295R cells were grown to near confluence in growth medium (DMEM/F12 supplemented with 1% ITS containing insulin, transferring, selenium, and linoleic acid, 2.5% NuSerum, and Pen/Strep). The growth medium was replaced with an assay medium that promotes cortisol synthesis (DMEM/F12 supplemented with 0.1% ITS and 20 µM forskolin) along with either (R)-etomidate, MOC-(R)-etomidate, or their metabolites (or nothing for controls). After allowing 48 hrs for forskolin-stimulated cortisol synthesis, 1.2 ml of the assay medium was collected, centrifuged (to remove cells and debris), and the cortisol concentration in the supernatant measured by an ELISA.

Figure 6:
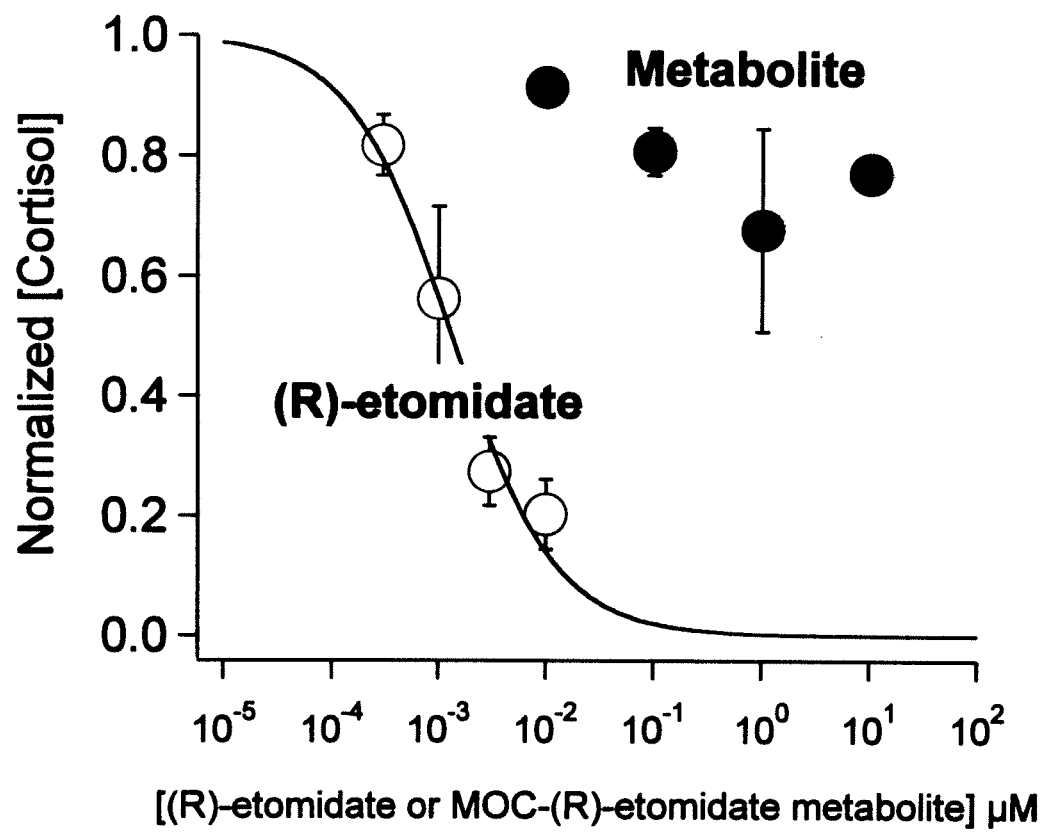
FIG. 6 shows a graph demonstrating that (R)-etomidate inhibits cortisol synthesis by H295R adrenocortical cells even at nanomolar concentrations (IC50=1.3±0.22 nM) whereas MOC-(R)-etomidate's metabolite has relatively little inhibitory activity even at micromolar concentrations. Each point represents the average cortisol concentration in 3 wells. The error bars are the standard deviations.

FIG. 6 compares the inhibitory action of (R)-etomidate and MOC-(R)-etomidate's metabolite on cortisol synthesis by H295R cells. The concentration of (R)-etomidate required to reduce the cortisol concentration in the assay medium by 50% (i.e. the IC50) was 1.3±0.2 nM whereas that for MOC-(R)-etomidate's metabolite was at least 1000-fold higher as even 1 µM failed to reduce the cortisol concentration in the assay medium by 50%. This indicates that MOC-(R)-etomidate's metabolite has no significant inhibitory action on cortisol synthesis by H295R cells.

Example 10

MOC-(R)-Etomidate is a Potent and Ultra-Short Acting General Anesthetic in Rats Rats were briefly restrained in a 3 inch diameter, 9 inch long acrylic chamber with a tail exit port. The desired dose of anesthetic was injected through a lateral tail vein catheter followed by an approximately 1 ml normal saline flush. Immediately after injection, rats were removed from the restraint device and turned supine. A rat was judged to have LORR if it failed to right itself (onto all four paws) within 5 sec of drug administration. A stop-watch was used to measure the duration of LORR, which was defined as the time from drug injection until the animal spontaneously righted itself. The $ED_{50}$ for LORR upon bolus anesthetic administration was determined from the anesthetic dose-dependence of LORR.

FIG. 7A shows the propofol, etomidate, and MOC-(R)-etomidate dose-response relationships for LORR in rats. The fraction of rats that had LORR increased with anesthetic dose. At the highest doses, all rats were anesthetized and there was no obvious anesthetic toxicity. From these data, the $ED_{50}$s for LORR following bolus administration of etomidate, propofol, and MOC-(R)-etomidate were determined to be 1.00±0.03 mg/kg (n=18), 4.1±0.3 mg/kg (n=20), and 5.2±1 mg/kg (n=20), respectively. At doses sufficient to produce LORR in rats, all three anesthetics produced LORR within several seconds of IV bolus administration. The duration of LORR (measured as the time required for a rat to regain consciousness and turn over onto all four paws) increased approximately linearly with the logarithm of the anesthetic dose (FIG. 7B); however, the slope of this relationship, which depends upon the anesthetic's half-life in the brain, was an order of magnitude lower for MOC-(R)-etomidate (2.8±0.4) than for etomidate (27±7) or propofol (22±4). The slopes for etomidate and propofol were not significantly different from one another. From this data it is evident that at equianesthetic doses, the duration of LORR was ~10-fold shorter for MOC-(R)-etomidate versus propofol or (R)-etomidate.

Example 13

Figure 8:
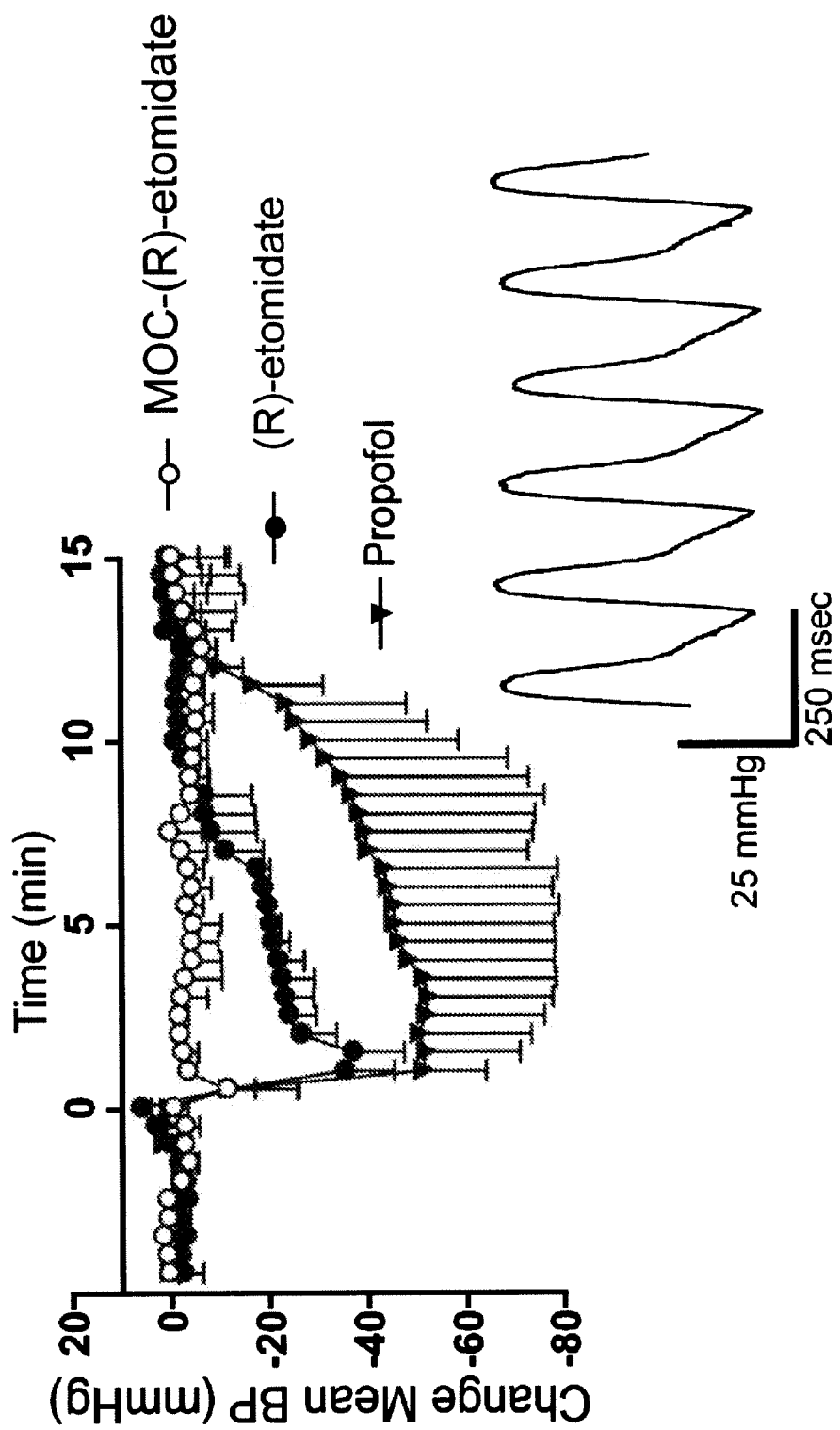
FIG. 8 shows a plot over time of mean blood pressure in rats following administration of equianesthetic doses of propofol, (R)-etomidate, and MOC-(R)-etomidate and demonstrates that MOC-(R)-etomidate depresses blood pressure significantly less than propofol or (R)-etomidate. Each point represents the mean during a 30 sec. epoch. The error bars are the standard deviations. Inset shows a representative arterial blood pressure trace prior to anesthetic administration.

MOC-(R)-Etomidate has Superior Hemodynamic Stability as Compared to Propofol and (R)-Etomidate Etomidate is often chosen for anesthetic induction over other agents in the critically ill patient because it better preserves hemodynamic stability. To determine whether MOC-(R)-etomidate similarly preserves hemodynamic stability, we measured and compared the actions of propofol, etomidate, MOC-(R)-etomidate, and vehicle (35% v/v propylene glycol in water) on heart rate and blood pressure in rats. To compare these drugs at equianesthetic doses, each was administered intravenously at twice its $ED_{50}$ for LORR (i.e., 2 mg/kg etomidate, 10 mg/kg MOC-(R)-etomidate, and 8 mg/kg propofol). The volume of propylene glycol administered was the same for vehicle, etomidate, and MOC-(R)-etomidate groups. Following animal acclimatization, data were recorded for 5 min prior to (baseline) and for 15 min after drug/vehicle injection (FIG. 8). Rats in each group had similar mean heart rates and blood pressure at baseline over the first 5 minutes (391±49 beats per minute (BPM), 118±9 mmHg). Vehicle caused no significant change in mean blood pressure relative to baseline (5±11 mmHg, n=3, at 90 sec); data not shown in FIG. 9 for clarity. However, MOC-(R)-etomidate, etomidate, and propofol (n=3 animals each) each caused a significant decrease in mean blood pressure relative to baseline and to each other in this rank order for both maximum magnitude (-11±15 mmHg, -36±11 mmHg, and -51±19 mmHg, respectively) and duration of significant effect (30 sec, 6.5 min, and 7 min, respectively). For all groups, vehicle (36+/-14 BPM), MOC-(R)-etomidate (24±33 BPM), etomidate (49±67 BPM), and propofol (64±56 BPM), there was a small, transient and variable increase in heart rate shortly after injection.

Example 14

Unlike (R)-Etomidate, MOC-(R)-Etomidate Does Not Suppress Adrenocortical Function 30 min After Administration Methods for study of rat adrenal function were adapted and optimized from several previously published reports. Immediately following weighing and IV catheter placement, dexamethasone (0.2 mg/kg IV; American Regent, Shirley, N.Y.) was administered to each rat to inhibit endogenous adrenocorticotropic hormone (ACTH) release, to suppress baseline corticosterone production, and to inhibit the variable stress response to restraint and handling. The IV tail vein catheter, used for both drug administration and blood draws, was heparin-locked after each use with 10 U/ml heparin to maintain patency; the heparin locking solution was "wicked" out of the catheter prior to drug administration and blood draws to minimize rat and sample heparinization. All blood draws were approximately 0.3 mls in volume. All drugs administrations were followed by a 1 ml normal saline flush to assure complete drug delivery.

Two hours following dexamethasone treatment, blood was drawn (for baseline measurement of serum corticosterone concentration) and a second dose of dexamethasome (0.2 mg/kg) was administered along with either intravenous anesthetic or vehicle (35% propylene glycol v/v in water) as a control. Fifteen minutes later, $ACTH_{1-24}$ (25 µg/kg; Sigma-Aldrich Chemical Co, St. Louis, Mo.) was given intravenously to stimulate corticosterone production. Fifteen minutes after $ACTH_{1-24}$ administration (i.e., 30 min after anesthetic or vehicle administration), a second blood sample was drawn to measure the $ACTH_{1-24}$-stimulated serum corticosterone concentration. $ACTH_{1-24}$ was dissolved in 1 mg/ml in deoxygenated water as stock, aliquoted, and frozen (-20° C.); a fresh aliquot was thawed just prior to each use. Rats in all three groups (vehicle, etomidate, and MOC-(R)-etomidate) received the same volume of propylene glycol.

Blood samples were allowed to clot at room temperature (10 to 60 min) before centrifugation at 3500 g for 5 min. Serum was carefully expressed from any resulting superficial fibrin clot using a clean pipette tip prior to a second centrifugation at 3500 g for 5 min. Following the second centrifugation, the resultant straw colored, clot-free serum layer was transferred to a fresh vial for a final, high-speed centrifugation (16000 g, for 5 min) to pellet any contaminating red blood cells or particulates. The serum was transferred to a clean vial and promptly frozen (-20° C.) pending corticosterone measurement within 1 to 2 days. Following thawing and heat inactivation of corticosterone binding globulins (65° C. for 20 min), serum baseline and $ACTH_{1-24}$ stimulated corticosterone concentrations were quantified using an Enzyme-Linked ImmunoSorbent Assay (ELISA) (Diagnostic Systems Laboratories, Webster, Tex.) and a 96-well plate reader (Molecular Devices, Sunnyvale, Calif.).

Figure 9:
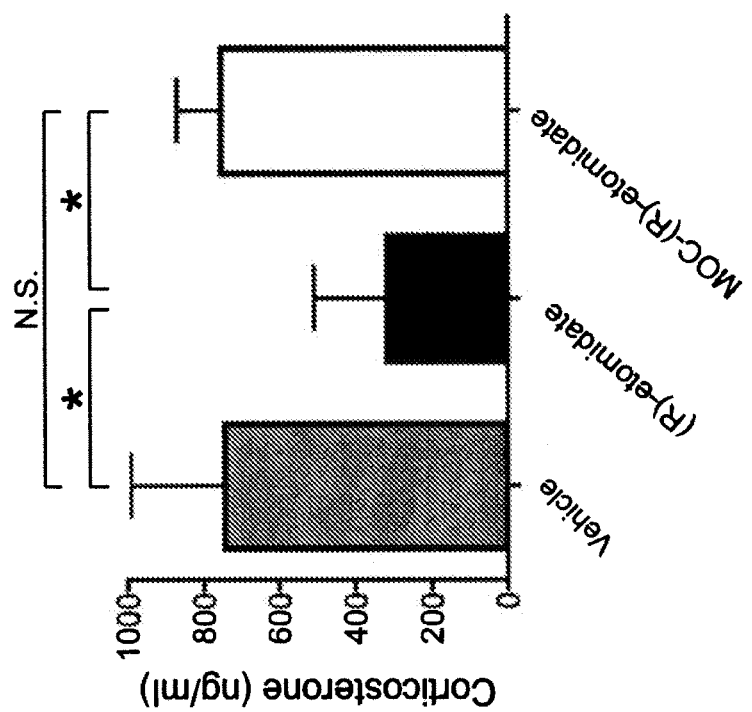
FIG. 9 shows that the plasma concentration of corticosterone (an adrenocortical steroid) was unchanged versus control (propylene glycol vehicle) 30 minutes after administration of MOC-(R)-etomidate whereas it was significantly reduced by an equianesthetic dose of (R)-etomidate. In these rats, corticosterone production was stimulated with ACTH$_{1-24}$ 15 minutes after anesthetic or vehicle administration and then plasma corticosterone concentrations were measured 15 minutes later. The error bars are the standard deviations.

Injection of $ACTH_{1-24}$ stimulated adrenocortical steroid production as all rats had significantly higher serum corticosterone concentrations fifteen minutes after $ACTH_{1-24}$ administration. However FIG. 9 shows that rats that had received (R)-etomidate fifteen minutes prior to $ACTH_{1-24}$ stimulation had significantly lower serum corticosterone concentrations than those that had received either vehicle or an equianesthetic dose of MOC-(R)-etomidate. In contrast, rats that had received MOC-(R)-etomidate had serum corticosterone concentrations that were not different from those that had received only vehicle.

Example 15

Summary of MOC-(R)-Etomidate

MOC-(R)-etomidate is a well-tolerated (R)-etomidate analogue that retains (R)-etomidate's important favorable pharmacological properties including rapid onset of action, high anesthetic potency, and hemodynamic stability. Like (R)-etomidate, it potently enhances $GABA_A$ receptor function, which is the presumed mechanism for producing anesthesia. However in contrast to (R)-etomidate, MOC-(R)-etomidate is very rapidly metabolized, ultra-short acting, and does not produce prolonged adrenocortical suppression following IV bolus administration.

MOC-(R)-etomidate is a "soft analogue" of (R)-etomidate. A soft analogue is a derivative of a parent compound that is specifically designed to undergo rapid and predictable metabolism after exerting its therapeutic actions. Commonly used soft analogues include the opioid remifentanil and the β-blocker esmolol. Both of these compounds contain labile carboxylate ester moieties that are rapidly hydrolyzed to carboxylic acids by esterases found in various organs and/or blood. The elimination half-life of these two drugs in humans is 1-2 orders of magnitude shorter than their non-ester containing analogues fentanyl and propranolol. (R)-etomidate also contains a carboxylate ester moiety that is hydrolyzed by liver esterases to a carboxylic acid, but it is a poor substrate for these esterases as reflected by its several hour elimination half-life. Comparison of the structures of remifentanil and esmolol with that of (R)-etomidate suggests two reasons for (R)-etomidate's slow rate of ester hydrolysis. First, the ester moiety in (R)-etomidate is attached directly to its imidazole ring whereas the labile ester moieties in remifentanil and esmolol are attached to ring structures via a spacer composed of two $CH_2$ groups. This spacer may be critical because it reduces steric hindrance, allowing esterases freer access to the carbonyl group. In support of this, as esmolol's spacer is decreased in length, its rate of ester hydrolysis decreases. Second, the electrons in (R)-etomidate's carbonyl group contribute to a π-electron system that extends into the imidazole ring. This reduces the carbonyl carbon's partial positive charge, making it a poorer substrate for nucleophilic attack by esterases. Based on this reasoning, we developed the strategy of adding a new ester moiety to (R)-etomidate that is both sterically unhindered and electronically isolated from the π-electron systems in the imidazole ring to produce an (R)-etomidate analogue that would be rapidly metabolized. We expected that this ester moiety, like those in remifentanil and esmolol, would be rapidly hydrolyzed by esterases present in various tissues and/or blood. This was confirmed by our in-vitro metabolic studies of MOC-(R)-etomidate showing that this moiety was rapidly metabolized to a carboxylic acid in pooled human S9 liver fraction, a commonly used in vitro drug biotransformation assay.

Our studies demonstrated that MOC-(R)-etomidate is a general anesthetic in two species. It has an anesthetic potency that is $1/4^{th}$-$1/5^{th}$ of (R)-etomidate's potency and likely produces anesthesia via the same receptor mechanism (i.e. by enhancing $GABA_A$ receptor function). Our rat studies further demonstrated that MOC-(R)-etomidate is an ultra-short acting anesthetic even when given at large multiples of its $ED_{50}$ for LORR. Anesthetic recovery from IV bolus administration of propofol and (R)-etomidate is considered to reflect redistribution of drug from the brain to other tissues rather than metabolism. Therefore, the similar slopes in the relationship between the duration of LORR and the logarithm of the anesthetic dose (FIG. 7B) suggests that propofol and (R)-etomidate redistribute from the brain at similar rates. The much faster recovery from anesthesia and shallower slope of this relationship with MOC-(R)-etomidate suggests that ultra-rapid metabolism contributes significantly to the termination of MOC-(R)-etomidate's anesthetic action.

MOC-(R)-etomidate produced a correspondingly brief (30 s) reduction in blood pressure, suggesting that MOC-(R)-etomidate's hemodynamic effects also terminate upon metabolism. In addition, we found that the maximum magnitude of this reduction was significantly less following administration of MOC-(R)-etomidate than following administration of equianesthetic doses of (R)-etomidate or propofol.

In common with other hydrophobic imidazole-containing compounds, (R)-etomidate suppresses adrenocortical steroid production. The primary mechanism underlying this suppression is inhibition of 11β-hydroxylase, a critical enzyme in the biosynthetic pathway leading to adrenocortical synthesis of cortisol, corticosterone, and aldosterone. It has been hypothesized that (R)-etomidate inhibits 11β-hydroxylase by competing with steroid precursors at the enzyme's presumably hydrophobic catalytic site. Because MOC-(R)-etomidate was designed to be rapidly metabolized by esterases to a highly polar carboxylic acid, we expected that MOC-(R)-etomidate would not produce prolonged adrenocortical suppression following administration. This expectation was realized as thirty minutes after administration, MOC-(R)-etomidate produced no reduction in the $ACTH_{1-24}$-stimulated serum corticosterone concentration whereas an equianesthetic dose of (R)-etomidate significantly reduced it. Our results also imply that any effect of MOC-(R)-etomidate's rapidly formed metabolite(s) on corticosterone synthesis is negligible following administration of a single intravenous dose.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

One skilled in the art would also readily appreciate that the present invention is well adapted to carry out the objects and obtain the ends and advantages mentioned, as well as those inherent herein. The molecular complexes and the methods, procedures, treatments, molecules, specific compounds described herein are presently representative of preferred embodiments, are exemplary, and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed:

1. A compound according to formula (I)

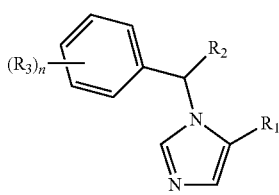

wherein, $R_1$ is $L_1C(O)OL_2C(O)OT$;

$R_2$ is a substituted or unsubstituted $C_1$-$C_{10}$ alkyl, $C_2$-$C_{10}$ alkenyl, or $C_2$-$C_{10}$ alkynyl, or $R_1$;

n is an integer from 0-5;

each $R_3$ is independently halogen or $R_2$;

$L_1$ and $L_2$ are each independently a bond, a substituted or unsubstituted $C_1$-$C_{10}$ alkylene, $C_2$-$C_{10}$ alkenylene, or $C_2$-$C_{10}$ alkynylene, wherein the backbone of alkylene may contain one or more heteroatoms;

T is H, a substituted or unsubstituted $C_1$-$C_{10}$ alkyl, $C_2$-$C_{10}$ alkenylene, $C_2$-$C_{10}$ alkynylene, nitrophenol, or cyclopropyl, wherein the backbone of alkyl may contain one or more heteroatoms; and pharmaceutically acceptable salts, stereoisomer mixtures, and enantiomers thereof.

2. The compound of claim 1, wherein said compound is present in the form of a pure enantiomer.

3. The compound of claim 2, wherein said enantiomer is the R enantiomer.

4. The compound of claim 1, wherein at least one of $R_2$, T, $L_1$, and $L_2$ are further substituted with one or more electron withdrawing groups.

5. The compound of claim 4, wherein said electron withdrawing group is a halogen.

6. The compound of claim 1, wherein the compound contains two or more ester groups.

7. The compound of claim 1, wherein $R_1$ is $L_1C(O)OL_2C(O)OT$, $R_2$ is $CH_3$, n is 0, $L_1$ is a bond, $L_2$ is $CH_2CH_2$, and T is $CH_3$.

8. The compound of claim 1, wherein $R_1$ is $L_1C(O)OL_2C(O)OT$, $R_2$ is $CH_3$, n is 0, $L_1$ is a bond, $L_2$ is $CH_2(CH_2)_4CH_2$, and T is $CH_2CH_2CH_2CH_3$.

9. The compound of claim 1, wherein $R_1$ is $L_1C(O)OL_2C(O)OT$, $R_2$ is $CH_3$, n is 0, $L_1$ is a bond, $L_2$ is $CH_2CH_2O(CH_2)_3$, and T is $CH_2CH_2OCH_3$.

10. The compound of claim 1, wherein $R_1$ is $L_1C(O)OL_2C(O)OT$, $R_2$ is $CH_3$, each $R_3$ is independently a halogen, n is 1-5, $L_1$ is a bond, $L_2$ is $CH_2CH_2$, and T is $CH_3$.

11. The compound of claim 10, wherein $R_1$ is $L_1C(O)OL_2C(O)OT$, $R_2$ is $CH_3$, each $R_3$ is fluorine, n is 1-5, $L_1$ is a bond, $L_2$ is $CH_2CH_2$, and T is $CH_3$.

12. The compound of claim 10, wherein $R_1$ is $L_1C(O)OL_2C(O)OT$, $R_2$ is $CH_3$, each $R_3$ is fluorine, n is 3, $L_1$ is a bond, $L_2$ is $CH_2CH_2$, and T is $CH_3$.

13. A compound of formula (I):

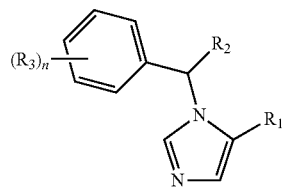

wherein $R_1$ is $L_1C(O)OT$, $R_2$ is $CH_3$, $R_3$ is $CH_2CH_2C(O)OCH_3$, n is 1, $L_1$ is a bond, and T is $CH_2CH_3$, and pharmaceutically acceptable salts, stereoisomer mixtures, and enantiomers thereof.

14. The compound of claim 1, wherein $R_1$ is $L_1C(O)OL_2C(O)OT$, $R_2$ is $CH_3$, $R_3$ is $CH_2CH_2C(O)OCH_3$, n is 1, $L_1$ is a bond, $L_2$ is $CH_2CH_2$, and T is $CH_3$.

15. A compound of formula (I):

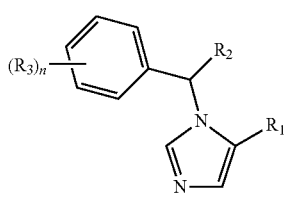

wherein $R_1$ is $L_1C(O)OT$, $R_2$ is $CH_2CH_2C(O)OCH_3$, n is 0, $L_1$ is a bond, and T is $CH_2CH_3$, and pharmaceutically acceptable salts, stereoisomer mixtures, and enantiomers thereof.

16. A compound of formula (I):

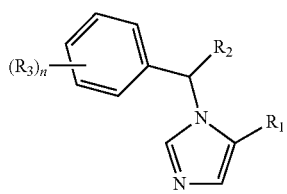

wherein $R_1$ is $L_1C(O)OT$, $R_2$ is $CH_3$, n is 0, $L_1$ is $CH_2CH_2$, and T is $CH_2CH_3$, and pharmaceutically acceptable salts, stereoisomer mixtures, and enantiomers thereof.

17. A pharmaceutical composition comprising a pharmaceutically effective amount of a compound according to formula (I)

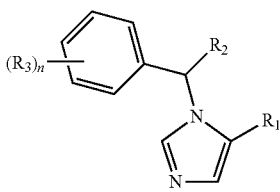

wherein, $R_1$ is $L_1C(O)OL_2C(O)OT$;

$R_2$ is a substituted or unsubstituted $C_1$-$C_{10}$ alkyl, $C_2$-$C_{10}$ alkenyl, or $C_2$-$C_{10}$ alkynyl, or $R_1$;

n is an integer from 0-5;

each $R_3$ is independently halogen or $R_2$;

$L_1$ and $L_2$ are each independently a bond, a substituted or unsubstituted $C_1$-$C_{10}$ alkylene, $C_2$-$C_{10}$ alkenylene, or $C_2$-$C_{10}$ alkynylene, wherein the backbone of alkylene may contain one or more heteroatoms;

T is H, a substituted or unsubstituted $C_1$-$C_{10}$ alkyl, $C_2$-$C_{10}$ alkenylene, $C_2$-$C_{10}$ alkynylene, nitrophenol, or cyclopropyl, wherein the backbone of alkyl may contain one or more heteroatoms; and pharmaceutically acceptable salts, stereoisomer mixtures, and enantiomers thereof, and a pharmaceutically acceptable carrier.

18. A method for providing anesthesia to a mammal comprising administering to said mammal a compound of formula (I) according to claim 1.

19. A method for providing anesthesia to a mammal comprising administering to said mammal a pharmaceutical composition according to claim 17.

20. The method of claim 18, wherein the composition comprises a compound of formula (I), wherein $R_1$ is $L_1C(O)OL_2C(O)OT$, $R_2$ is $CH_3$, n is 0, $L_1$ is a bond, $L_2$ is $CH_2CH_2$, and T is $CH_3$.

21. The method of claim 18, wherein the administration step administers 0.01 to 100 mg/kg of the compound of formula (I).

22. The method of claim 18, wherein said administering comprises: injection of a single effective dose of the compound of formula (I).

23. The method of claim 18, wherein said administering comprises: continuous infusion of an effective dose of the compound of formula (I).

24. The method of claim 18, wherein the method further comprises administering to the mammal an effective amount of a therapeutic agent selected from another sedative hypnotic agent, an analgesic agent, and a paralytic agent.

* * * * *

UNITED STATES PATENT AND TRADEMARK OFFICE
CERTIFICATE OF CORRECTION

PATENT NO.       : 8,557,856 B2                                                Page 1 of 1
APPLICATION NO. : 12/935086
DATED            : October 15, 2013
INVENTOR(S)      : Raines et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 468 days.

Signed and Sealed this

Fifteenth Day of September, 2015

Michelle K. Lee
*Director of the United States Patent and Trademark Office*